United States Patent [19]
Sciulli

[11] Patent Number: 5,487,738
[45] Date of Patent: Jan. 30, 1996

[54] APPARATUS FOR DRAWING FLUIDS INTO A HYPODERMIC SYRINGE

[76] Inventor: Eugene B. Sciulli, 1024 N. Shore Dr. NE., St. Petersburg, Fla. 33701-1440

[21] Appl. No.: 414,436

[22] Filed: Mar. 31, 1995

[51] Int. Cl.⁶ .................................................. A61B 19/00
[52] U.S. Cl. .............................. 604/414; 604/187; 141/27
[58] Field of Search ................................... 604/411, 414, 604/187, 207, 208; 141/27, 28, 97, 383, 386

[56] References Cited

U.S. PATENT DOCUMENTS

| | | | |
|---|---|---|---|
| 2,677,372 | 5/1954 | Barnish, Jr. | 604/414 |
| 3,853,158 | 12/1974 | Whitty | 604/414 X |
| 3,875,979 | 4/1975 | Hults | 604/414 X |
| 4,518,387 | 5/1985 | Murphy et al. | 604/187 |
| 4,883,101 | 11/1989 | Strong | 141/27 |
| 5,247,972 | 9/1993 | Tetreault | 141/27 |

*Primary Examiner*—John D. Yasko

[57] ABSTRACT

An apparatus for drawing fluid into a hypodermic syringe comprising a hypodermic syringe of the type having a cylindrical container, the hypodermic syringe having an open proximal end and a distal end with a needle and a shoulder at the proximal end, the hypodermic syringe also having a reciprocable rod with a distal end formed with a piston positioned interior of the container and a proximal end with a plunger; a holder having a distal end and a proximal end and a central extent therebetween, the proximal end having a planar surface provided with a forward stop perpendicular thereto, the distal end having an upper support surface; and a reciprocable platform having a proximal end and a distal end with a lower horizontal surface slidable upon the upper surface of the proximal end of the holder, the platform also having an upper surface; the platform also having an upturned distal end adapted to limit the withdrawal movement of a plunger, the platform also having a recess at a central extent adapted to receive a portion of the hypodermic syringe to preclude axial movement thereof.

8 Claims, 6 Drawing Sheets

APPARATUS FOR DRAWING FLUIDS INTO A HYPODERMIC SYRINGE

BACKGROUND OF THE INVENTION

1. Field of the Invention

The present invention is a portable device for filling a hypodermic syringe and, more particularly, for drawing medicinal fluids into hypodermic syringes with great accuracy and safety by persons with a minimum of training including those persons with manual and visual disabilities.

2. Description of the Prior Art

The technique for filling a hypodermic syringe requires one to first draw air into the syringe by pulling the plunger part way out. One must then aim for, and finding it, push the sharp needle of the syringe through the 3/16 diameter rubber top of a vial. The syringe plunger is then depressed to inject the air into the vial to fill the partial void that will occur when fluid is later drawn out. At this point it is necessary to lift and turn the syringe/vial assembly to a near vertical position with the vial uppermost and, holding the vial and syringe firmly while keeping the syringe needle point below the fluid surface, slowly retract the plunger all the time determining the quantity of liquid being withdrawn by reading the markings on the vial body as the end of the plunger slides by.

The technique described is used by medical professionals and is that taught, or shown, to diabetics and other patients requiring self-administered injections. Many such persons do not have the manual dexterity, eyesight and/or other necessary abilities to properly fill the syringe and may accidentally prick themselves or even dull the needle by striking hard surfaces of the vial. Even the most experienced professionals may occasionally suffer those same accidents.

In this respect, the device for drawing fluid into a hypodermic syringe according to the present invention substantially departs from the conventional concepts and designs of the prior art, and in so doing provides an apparatus primarily developed for the purpose of benefiting medical professionals as well as non-professionals who by lack of training, age, infirmities or traumatic fear experience difficulty in filling a hypodermic syringe.

Therefore, it can be appreciated that there exists a continuing need for a new and improved device for drawing fluid into a hypodermic syringe which can be used to benefit medical professionals and non-professionals alike because of its conveniences and safety features. In this regard, the present invention substantially fulfills this need.

There is on the market a simple-to-use fountain pen-like device. It requires only the screwing on of a new needle and twisting the pen parts to select the proper injection dosage and make the pen ready for use. This great convenience comes with a relatively high price tag and the pens are frequently lost or stolen.

Other devices now known differ from the present invention in that they do not load the syringe in preparation for an actual injection.

SUMMARY OF THE INVENTION

In view of the foregoing disadvantages inherent in the known types of hypodermic syringes and related devices now present in the prior art, the present invention provides an improved device for drawing fluid into a hypodermic syringe which most persons can use with a minimum amount of training. As such, the general purpose of the present invention, which will be described subsequently in greater detail, is to provide a new and improved device for drawing fluid into a hypodermic syringe and a method which has all the advantages of the prior art and none of the disadvantages.

To attain this, the present invention essentially comprises a new and improved apparatus for drawing fluid into a hypodermic syringe comprising, in combination, a hypodermic syringe of the type having a cylindrical container for fluids to be dispensed, the hypodermic syringe having an open proximal end and a distal end with a needle at the distal end and a shoulder at the proximal end, the hypodermic syringe also having a reciprocal rod with a distal end formed with a piston positioned interior of the container, the rod also having a proximal end with a plunger for reciprocating the piston for drawing fluids into the cylinder and the forcing of fluids therefrom; a vial having a closed cylindrical extent at its lower end and a neck of a reduced diameter with an opening at its upper end and a closure pierceable by a needle, the bottle also having a quantity of medicinal fluid therein for being drawn from the vial by a needle of a hypodermic syringe; a holder having a distal end and a proximal end and a central extent therebetween with a planar lower surface therebeneath, the distal end including an upper support surface adapted to support the vial of medicinal fluid, the support surface being formed at an angle of about 30 degrees with respect to the lower surface and sloping downwardly toward the central extent of the holder, the upper surface of the proximal end being planar and provided with a forward stop perpendicular to the upper surface; a reciprocable platform having a proximal end and a distal end with a lower horizontal surface slidable upon the upper surface at the proximal end of the holder, the platform also having an upper surface formed with a curvature adapted to receive thereon the hypodermic syringe, the platform also having an upturned distal end adapted to limit the withdrawal movement of the plunger, the platform also having a recess at a central extent adapted to receive the shoulder to preclude axial movement thereof; and a base having a planar upper horizontal surface adapted to receive thereon the lower horizontal surface of the holder with coupling components therebetween.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved device for drawing fluid into a hypodermic syringe which most persons can use with a minimum amount of training which has all the advantages of the prior art hypodermic syringes and related devices and none of the disadvantages.

It is also an object of the present invention to provide a reliably constructed inexpensive device which is portable, but which can be fixed to enable successful use by persons with limited manual dexterity including loss of one hand.

It is a further object of the present invention to provide a magnifier and an adjustable stop to enable successful use by persons with limited visual acuity including total loss of eyesight.

Another object of the present invention is to assure that the hypodermic syringe needle not be damaged by touching any device part or surface other than the rubber closure of the vial and the syringe be held securely so the plunger can be operated in both the push and pull modes without accidental pricking of the operator.

Another object of the present invention is to hold the vial securely in a fixed position while permitting the vial to be rotated in its holder.

Another object of the present invention is to permit relative motion between the hypodermic syringe and vial so that the syringe needle will puncture the vial rubber closure and penetrate into the vial a distance predetermined by the angle of the vial relative to the syringe so that ultimately all but a few drops of medication will be withdrawn without formation of air bubbles in the syringe.

Another object of the present invention is to provide an apparatus for drawing fluid into a hypodermic syringe comprising a hypodermic syringe of the type having a cylindrical container, the hypodermic syringe having an open proximal end and a distal end with a needle and a shoulder at the proximal end, the hypodermic syringe also having a reciprocable rod with a distal end formed with a piston positioned interior of the container and a proximal end with a plunger for reciprocating the piston; a holder having a distal end and a proximal end and a central extent therebetween, the proximal end having a planar surface provided with a forward stop perpendicular thereto, the distal end having an upper support surface adapted to retain a vial of fluid fixed with respect to the upper surface of the proximal end; and a reciprocable platform having a proximal end and a distal end with a lower horizontal surface slidable upon the upper surface of the proximal end of the holder, the platform also having an upper surface adapted to receive thereon a hypodermic syringe with its needle facing the distal end of the holder, the platform also having an upturned distal end adapted to limit the withdrawal movement of a plunger of the hypodermic syringe, the platform also having a recess at a central extent adapted to receive a portion of the hypodermic syringe to preclude axial movement thereof.

Most of the foregoing objects can be accomplished by providing a vial holder set at an angle to a platform on which the hypodermic syringe is placed with its enlarged shoulder in a positioning slot so the syringe can be held in place by a cover containing a magnifier element. Relative motion between the vial and syringe, together with retraction of the syringe plunger, act to draw the medication into the syringe.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIGS. 10 and 11 show alternate embodiments of the invention for fixedly positioning the system on a support surface such as a table while FIG. 11A is a cross sectional view of the adjusting mechanisms taken axially through the screw of FIG. 11.

The same reference numerals refer to the same parts throughout the various Figures.

DESCRIPTION OF THE PREFERRED EMBODIMENT

Figure 1:
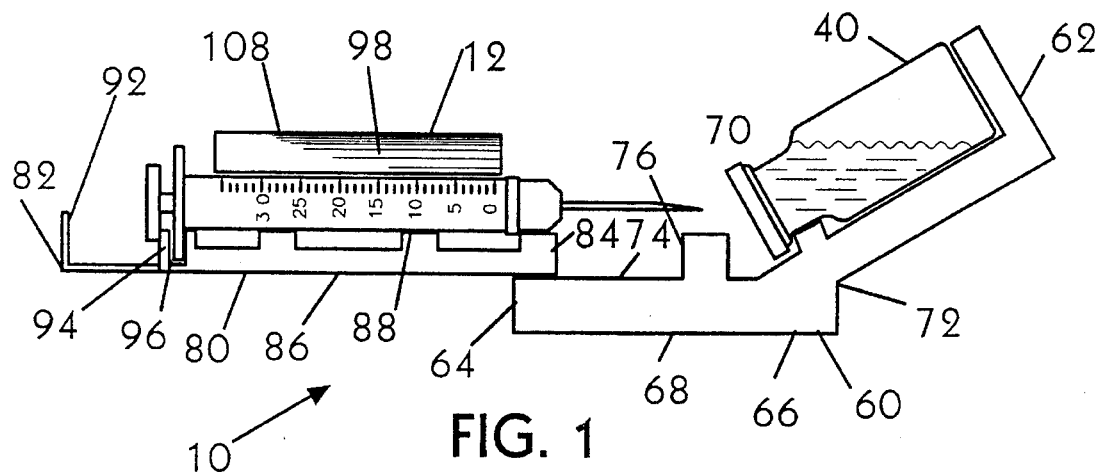
FIG. 1 is a schematic representation of the preferred embodiment of the device for drawing fluid into a hypodermic syringe constructed in accordance with the principles of the present invention which features a vial in a holder that is set at an angle to the hypodermic syringe set on a platform with a cover containing a magnifier which is positioned to hold the syringe firmly when the plunger is activated and also with adjustable stops which serve to limit travels.

With reference now to the drawings, and in particular to FIG. 1 thereof, the preferred embodiment of the new and improved device for drawing fluid into a hypodermic syringe embodying the principles and concepts of the present invention and generally designated by the reference numeral 10 will be described.

The present invention, the new and improved device for drawing fluid into a hypodermic syringe, is a system 10 comprised of a plurality of components. In their broadest context, the components include a hypodermic syringe, a vial, a holder and a platform, and in an alternate embodiment, a base. Each of the individual components is specifically configured and correlated one with respect to the other so as to attain the desired objectives.

The principle component of the system 10 of the present invention is a hypodermic syringe 12. This syringe is of the generally conventional type having a cylindrical container or vial 14. Such container is for the containing of fluids 16 taken from the vial 40. The hypodermic syringe has an open proximal end 18. It also has a distal end 20 with a needle 22 secured therethrough for the passage of fluids to and from the container. Also formed with respect to the syringe at the proximal end of the container is a shoulder 24. The shoulder is for being contacted by the fingers of the user to assist in usage of the device, i.e. making injections.

Figure 2:
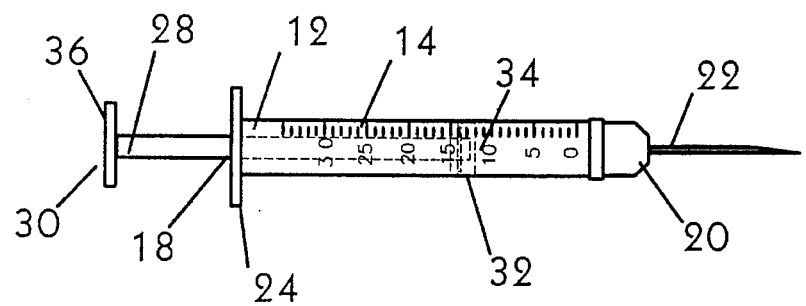
FIG. 2 shows a transparent body hypodermic syringe having a sharp pointed hollow needle with the enlarged shoulder on the body which provides a holding assistance when the plunger is pulled or pushed and with the graduated markings on the syringe body to indicate dosages that are read as the plunger is retracted.

As shown in FIG. 2, the hypodermic syringe also has a reciprocal rod 28 with a distal end 30 formed with a piston 32. The piston is adapted to be located interior of the container 14. The rod also has a proximal end 34 with a plunger 36 at its distal end. The function of the plunger is for being contacted by the thumb of a user for reciprocating the piston. The plunger thus functions by its reciprocation for drawing fluids into the cylinder and, upon depression, forcing fluids from the cylinder into the patient or the vial.

Figure 3:
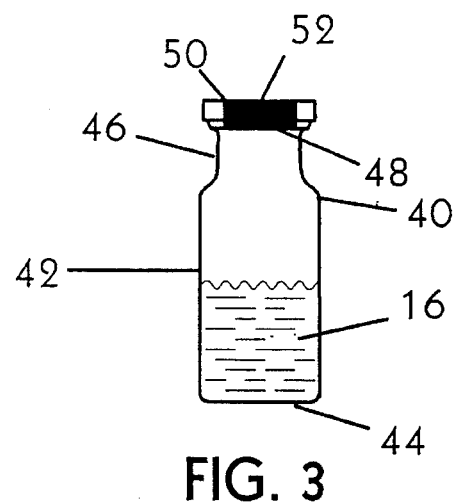
FIG. 3 shows a glass or rigid body vial containing fluid medication and a thin rubber or rubber-like mouth closure.

The next major component of the system 10 is a vial 40. Note FIG. 3. The vial is a small bottle-like container having a cylindrical extent 42 closed at its lower end 44. The vial also has a neck 46 of a reduced diameter with an opening 48 at its upper end 50. A closure 52 of a pierceable material, preferably rubber or other elastomeric material, natural or synthetic, is formed over the closure to seal the medicinal fluids within the vial. The vial closure is of the type of material to be pierced by a needle of the hypodermic syringe for withdrawing the fluids therefrom.

The vial is made to contain a quantity of medicinal fluid 16. The fluid is sealed within the vial for being dispensed when needed. The dispensing is by being drawn from the vial by a needle of the hypodermic syringe through the action of a reduced pressure or suction.

Next provided is a holder 60 which is best seen in FIG. 1. The holder has a distal end 62 and a proximal end 64. The holder also has a central extent 66 therebetween. A planar lower surface 68 is located at the lower surface of the holder. The distal end of the holder includes an upper support surface 70 with a curved configuration. The support surface includes an upwardly extending support plate for receiving the neck of the vial 40. The free upper ends of the support plate are preferably provided with rubber tips to create a holding force for the vial when positioned thereon. It is adapted to support the vial of medicinal fluids. That support surface is formed at an angle 72 of about thirty degrees with respect to the lower surface of the holder. The support surface slopes downwardly toward the central extent of the holder. In addition, the upper surface 74 at the proximal end of the holder is planar in configuration. It is provided with a forward stop 76 perpendicular to the upper surface thereadjacent. The function of the forward stop will be described hereinafter.

Next provided is a reciprocable platform 80. The reciprocable platform has a proximal end 82 and a distal end 84. It also has a lower horizontal surface 86. Such lower horizontal surface is adapted to slide upon and with respect to the upper surface 74 of the holder at the proximal end of the holder. The platform also has upper surfaces 88 formed with a curvature 90. Such curvature is adapted to receive thereon a hypodermic syringe 12 at its cylindrical central extent. The platform also has an upturned plate 92 adapted to limit the withdrawal movement of the plunger 36 from the syringe 12. The platform also has a recess 94 at a central extent 96. Such recess is adapted to receive the shoulder 24 of the hypodermic syringe to preclude its axial movement during operation and use.

As shown in the drawings, the device for drawing medication into a hypodermic syringe in accordance with the present invention is an assembly preferably made of a strong molded plastic material. The device is lightweight and fully portable. It can be operated with no restraints on a tabletop but is provided with a flat base with extension lugs which can be held in a semi-permanent condition with clamps, vacuum cups or other means, not shown, or alternately it can be permanently fixed with screws through holes in the lugs.

At one end of the present invention is the vial housing 62. This housing is set at a preferred angle relative to the base and hypodermic syringe. Note FIG. 1. The purpose of the angle is to present a vertical column of fluid higher than the hypodermic syringe needle so that nearly all the liquid can be withdrawn from the vial by the needle without drawing air or forming air bubbles in the syringe. The housing holds the vial securely while permitting it to be rotated so that the syringe needle will not always puncture the rubber closure at the same spot.

On the base is a moveable platform on which the hypodermic syringe is placed with the needle point closest to the vial and the widened shoulders of the syringe body in a slot so prepared that the volumetric graduation marks on the syringe body are in a position to be read.

Figure 4:
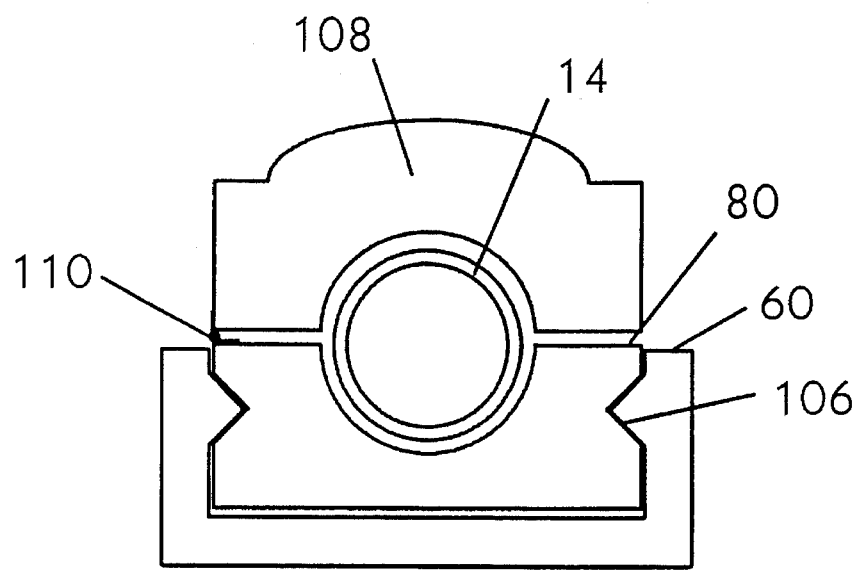
FIGS. 4 and 5 show the holder for retaining the hypodermic syringe on the reciprocating platform, both the closed and opened positions.
Figure 5:
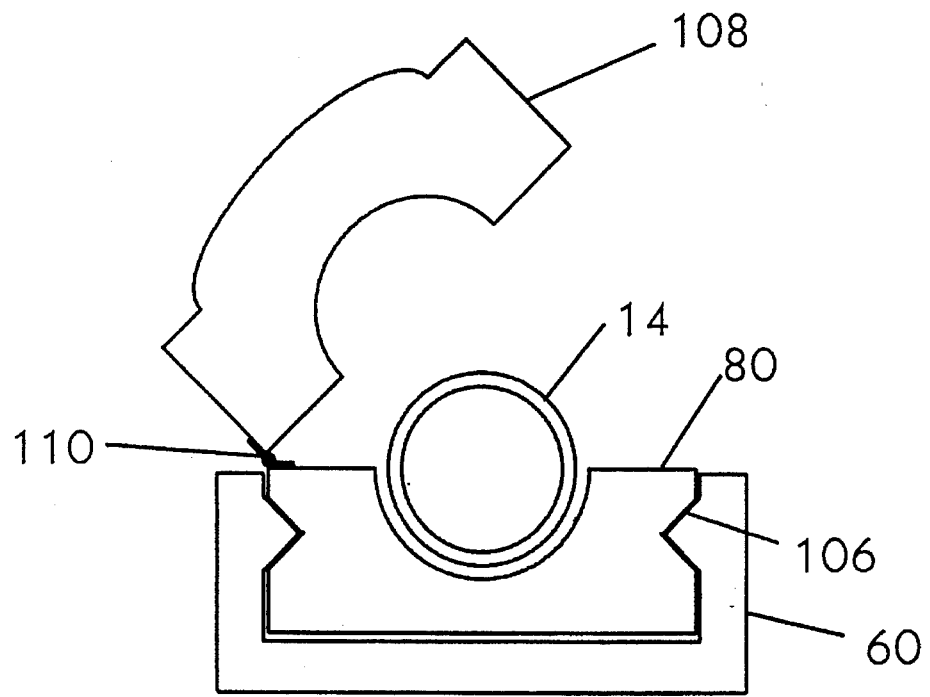
Figure 6A:
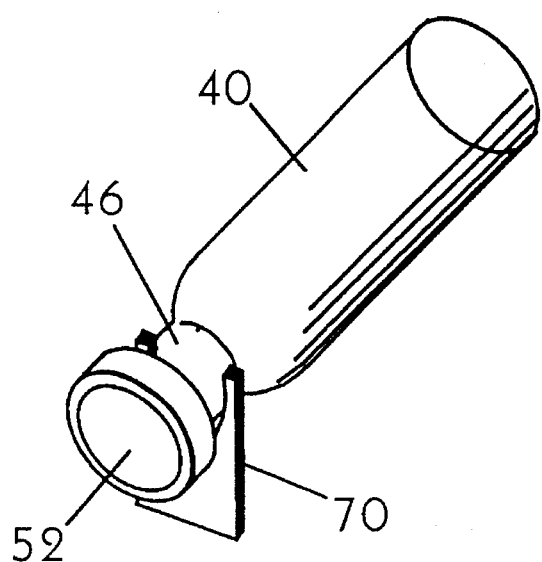
FIG. 6A, 6B, and 6C illustrate the support of the vial through the upper support surface of the holder.
Figure 6B:
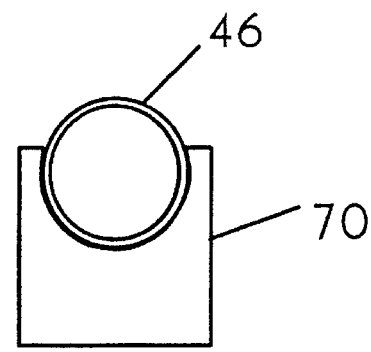
Figure 6C:
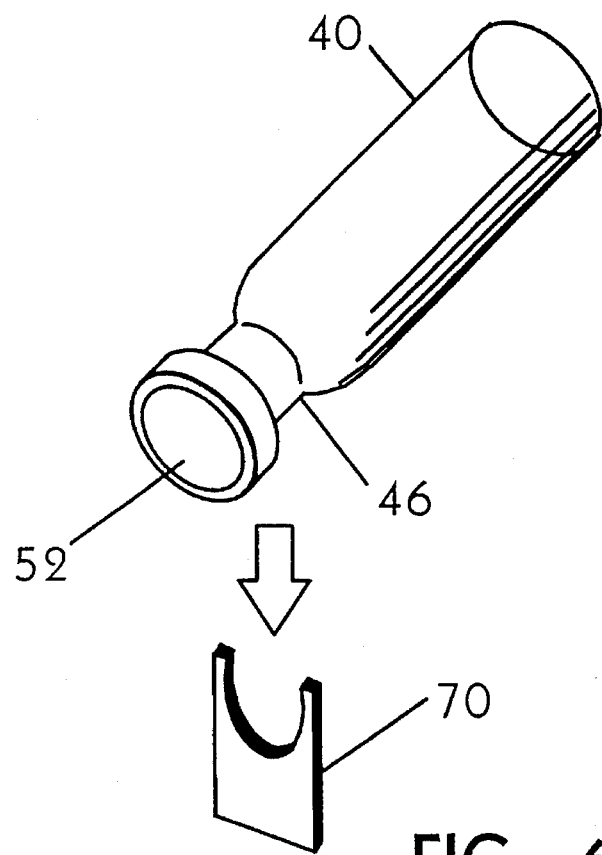

The holder 102 has a fixed lower member which is the reciprocating platform 80. The two members maintain the hypodermic syringe 12 in position during operation and use. A hinge 110 couples the upper and lower components to allow positioning and removal of the hypodermic syringe with respect to the reciprocating platform. It is in the upper component of the holder where the transparent magnifier 104 is located. Proper reciprocation is effected through mating V-shaped components forming a dovetail 106 between the upper and lower components. Note FIGS. 4 and 5.

The hypodermic syringe on its platform is restrained from moving by a holder 102 with included transparent magnifier 104 appropriately positioned to read the syringe body markings. In this condition the syringe plunger can be retracted to draw air into the syringe. Alternately a device with greater magnification can be attached to the invention using any convenient means including a magnifier glass on a holding rod screwed into the base.

Figure 7:
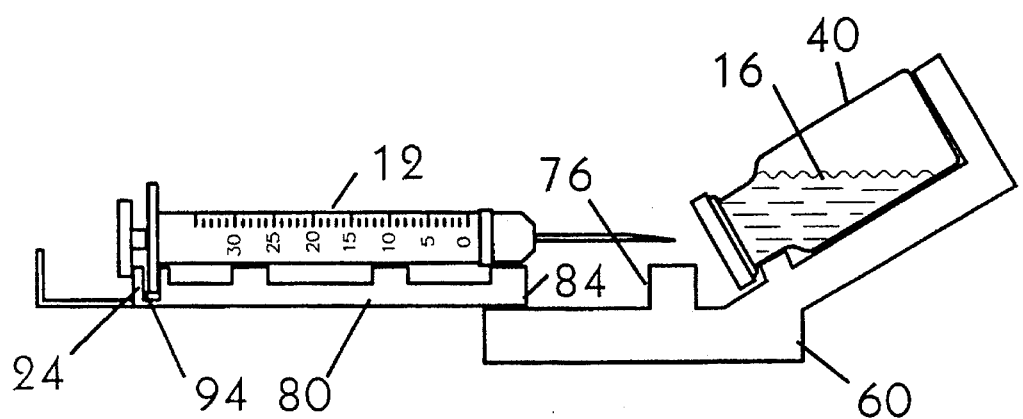
FIGS. 7, 8, and 9 illustrate in sequential fashion the filling of the hypodermic syringe with fluid from the vial.
Figure 8:
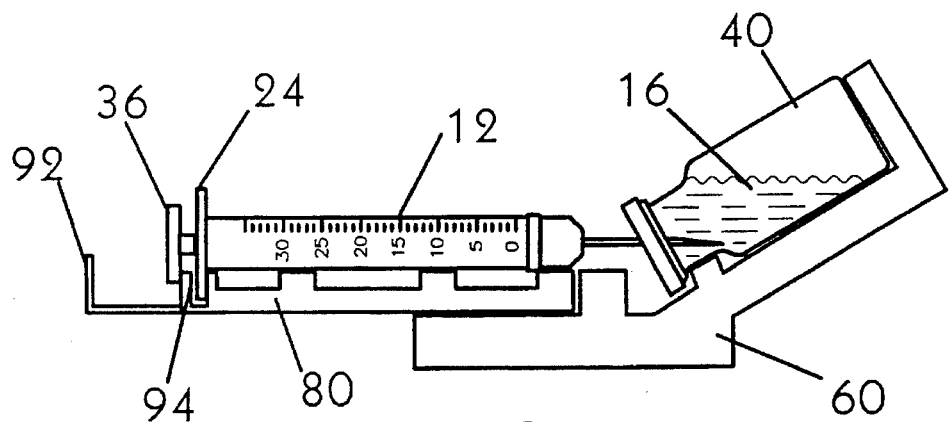
Figure 9:
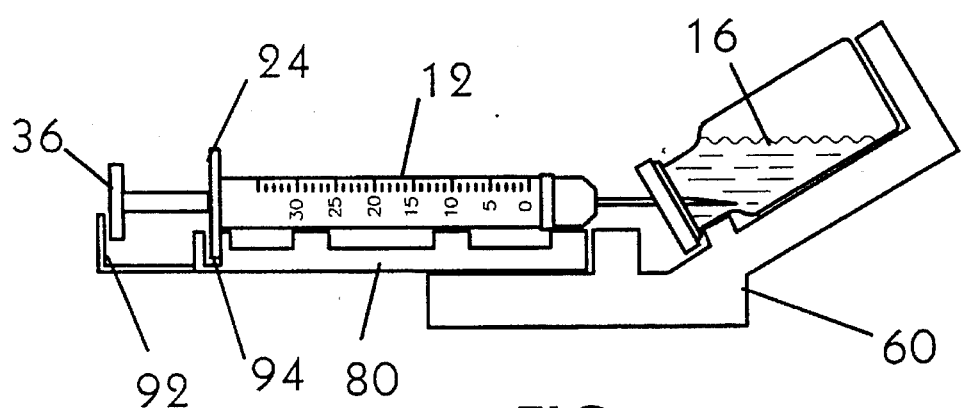

The operation of the device can be readily seen in FIGS. 7, 8 and 9. Note that the syringe with its plunger is retracted it is then slid on its platform until a stop is encountered. That motion is so controlled that the hypodermic syringe needle enters a 3/16 inch target area, punctures the rubber closure and penetrates a predetermined distance into the vial so that the needle point is continuously below the surface of the liquid in the vial. A slow push of the plunger injects the aforementioned air in the syringe into the vial to fill the partial void which will occur when fluid is withdrawn from the vial. Fluid withdrawal occurs when the plunger is retracted a predetermined distance equivalent to the medication dosage required. This dosage can be read on the syringe body with the aid of a magnifier or alternately can be preset by a stop to limit rearward travel of the plunger.

The hypodermic syringe preparation operation is concluded by moving the vial and/or syringe back to its original start position, removing the restraint on the syringe and lifting the syringe with retracted plunger from its platform.

Figure 10:
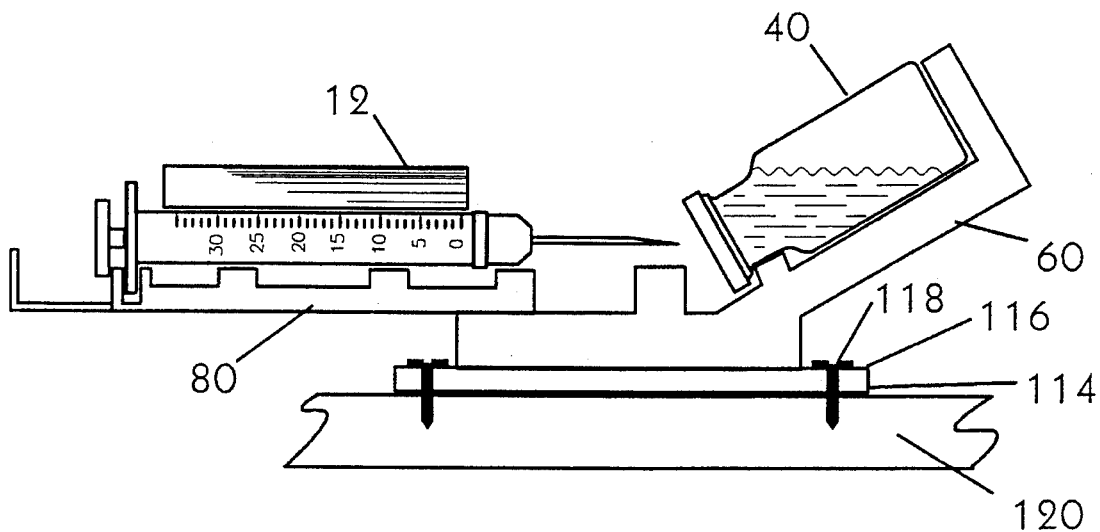

In an alternate embodiment of the invention as shown in FIG. 10, there is also included a base 114. The base is formed with a planar upper horizontal surface 116. It is adapted to receive thereon the lower horizontal surface 68 of the holder 60. Screws 118 couple the base and the holder with respect to a fixed member such as a table 120 for allowing usage of the system at a fixed location.

Figure 11:
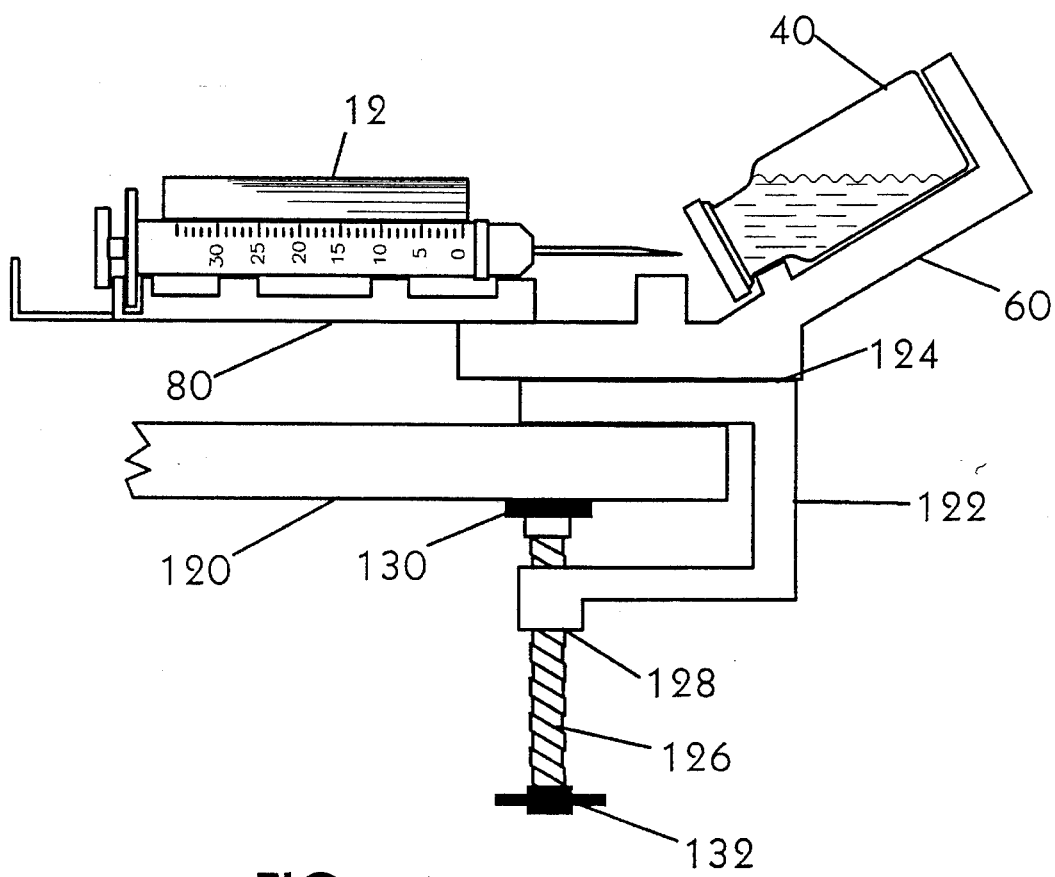

In yet a further embodiment, the screws 118 are eliminated and a C-clamp 122 is used with an upper surface 124 secured to the lower surface 68 of the holder 60. Note FIG. 11. A screw 126 is in threaded engagement with a threaded hole 128 in a lower portion of the C-clamp. The upper surface 130 of the screw advances or retracts through rotation of the handle 132 to tighten and loosen the C-clamp and, hence, the holder and system with respect to a tabletop surface 120 or the like. Note FIG. 11. The FIG. 11 embodiment also forms its stop member 92 with sliding and securement mechanisms. This permits the plate 134 with locking screw 135 to move with respect to the reciprocating platform which are coupled through a dove tail connection. This allows for the accurate filling of the syringe as a function of the stop member. Note FIG. 11A.

Figure 12:
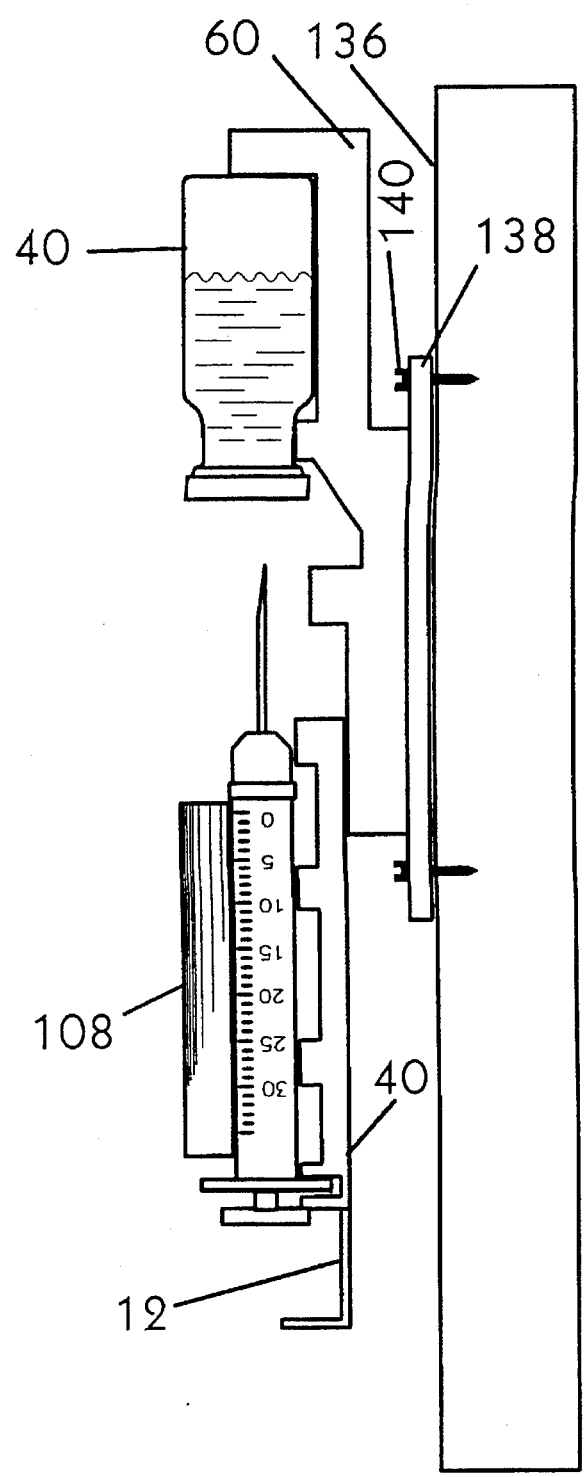
FIG. 12 is another alternate embodiment of the invention wherein the system is maintained in a vertical orientation with the hypodermic syringe and the vial being in essentially axial alignment.

The final embodiment of the invention is shown in FIG. 12. In such embodiment, the tabletop 120 is dispensed with and a vertical surface such as a wall 136 is utilized for holding the holder 60 in a fixed orientation. Such is effected through an intermediate plate 138 and screws 140 which effect the coupling therebetween. In such final embodiment, the hypodermic syringe has its central axis in near or essentially axial alignment with the axis of the vial. Further, the vial is held vertically and not at an angle with respect to the needle. The operation of the device is essentially the same as that which is described with respect to the primary and the other alternate embodiments.

It should be noted that distances, elevations, clearances, angles, motions, and other relationships of members are controlled during construction so that virtually all the medication will be withdrawn from the vial; the hypodermic syringe needle will never touch the vial and closure punctures will occur at random points.

The discussion notes that the hypodermic syringe on its platform is moved towards the vial but it should be obvious that relative motion is required and persons versed in the arts could devise means to keep the hypodermic syringe stationary and move the vial holder with its contents to the favored position required for closure puncture and needle penetration into the vial.

It should be noted that persons versed in the art may devise or design other holding means not specifically noted herein.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved apparatus for drawing fluid into a hypodermic syringe comprising, in combination:

a hypodermic syringe of the type having a cylindrical container for fluids to be dispensed, the hypodermic syringe having an open proximal end and a distal end with a needle at the distal end and a shoulder at the proximal end, the hypodermic syringe also having a reciprocal rod with a distal end formed with a piston positioned interior of the container, the rod also having a proximal end with a plunger for reciprocating the piston for drawing fluids into the cylinder and the forcing of fluids therefrom;

a vial having a closed cylindrical extent at its lower end and a neck of a reduced diameter with an opening at its upper end and a closure pierceable by a needle, the bottle also having a quantity of medicinal fluid therein for being drawn from the vial by a needle of a hypodermic syringe;

a holder having a distal end and a proximal end and a central extent therebetween with a planar lower surface therebeneath, the distal end including an upper support surface adapted to support the vial of medicinal fluid, the support surface being formed at an angle of about 30 degrees with respect to the lower surface and sloping downwardly toward the central extent of the holder, the upper surface of the proximal end being planar and provided with a forward stop perpendicular to the upper surface;

a reciprocable platform having a proximal end and a distal end with a lower horizontal surface slidable upon the upper surface at the proximal end of the holder, the platform also having an upper surface formed with a curvature adapted to receive thereon the hypodermic syringe, the platform also having an upturned distal end adapted to limit the withdrawal movement of the plunger, the platform also having a recess at a central extent adapted to receive the shoulder to preclude axial movement thereof; and a base having a planar upper horizontal surface adapted to receive thereon the lower horizontal surface of the holder with coupling components therebetween.

2. An apparatus for drawing fluid into a hypodermic syringe comprising:

a hypodermic syringe of the type having a cylindrical container, the hypodermic syringe having an open proximal end and a distal end with a needle and a shoulder at the proximal end, the hypodermic syringe also having a reciprocable rod with a distal end formed with a piston positioned interior of the container and a proximal end with a plunger for reciprocating the piston;

a holder having a distal end and a proximal end and a central extent therebetween, the proximal end having a planar surface provided with a forward stop perpendicular thereto, the distal end having an upper support surface adapted to retain a vial of fluid fixed with respect to the upper surface of the proximal end; and a reciprocable platform having a proximal end and a distal end with a lower horizontal surface slidable upon the upper surface of the proximal end of the holder, the platform also having an upper surface adapted to receive thereon a hypodermic syringe with its needle facing the distal end of the holder, the platform also having an upturned distal end adapted to limit the withdrawal movement of a plunger of the hypodermic syringe, the platform also having a recess at a central extent adapted to receive a portion of the hypodermic syringe to preclude axial movement thereof.

3. The apparatus as set forth in claim 2 and further including a base having a planar upper horizontal surface adapted to receive thereon the lower horizontal surface of the holder with coupling components therebetween.

4. The apparatus as set forth in claim 3 wherein the coupling components are screws.

5. The apparatus as set forth in claim 3 wherein the coupling components are a C-clamp.

6. The apparatus as set forth in claim 2 wherein the hypodermic syringe and vial are in a vertical orientation in essentially near alignment.

7. The apparatus as set forth in claim 2 and further including a clamping device to hold the hypodermic syringe resting on the platform with the clamping device having an integral magnifier to facilitate reading of graduations on the hypodermic syringe body.

8. The apparatus as set forth in claim 2 and further including an adjustable stop at the proximal end of the movable platform for precise loading of the hypodermic syringe by a person having deficient or total loss of sight.

* * * * *